United States Patent
Gallois-Bernos et al.

(10) Patent No.: US 11,096,919 B2
(45) Date of Patent: *Aug. 24, 2021

(54) ESTERS FOR TREATMENT OF OCULAR INFLAMMATORY CONDITIONS

(71) Applicant: Johnson & Johnson Vision Care, Inc., Jacksonville, FL (US)

(72) Inventors: Annabelle Gallois-Bernos, Jacksonville, FL (US); Frank F. Molock, Jr., Birmingham (GB); Carrie L. Davis, St. Augustine, FL (US); Kathrine Osborn Lorenz, Jacksonville, FL (US); James K. Young, Ponte Vedra Beach, FL (US); Kristy L. Canavan, Jacksonville, FL (US); Fang Lu, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/460,208

(22) Filed: Jul. 2, 2019

(65) Prior Publication Data

US 2019/0328698 A1 Oct. 31, 2019

Related U.S. Application Data

(63) Continuation of application No. 13/495,049, filed on Jun. 13, 2012, now Pat. No. 10,383,839.

(60) Provisional application No. 61/503,158, filed on Jun. 30, 2011.

(51) Int. Cl.
| | |
|---|---|
| *A61K 31/232* | (2006.01) |
| *A61K 31/557* | (2006.01) |
| *A61K 31/215* | (2006.01) |
| *A61K 31/5575* | (2006.01) |
| *A61K 31/661* | (2006.01) |
| *A61K 9/00* | (2006.01) |
| *A61K 31/16* | (2006.01) |
| *A61K 31/201* | (2006.01) |
| *A61K 31/202* | (2006.01) |
| *A61K 31/203* | (2006.01) |
| *A61K 31/683* | (2006.01) |
| *A61K 9/08* | (2006.01) |

(52) U.S. Cl.
CPC .......... *A61K 31/232* (2013.01); *A61K 9/0048* (2013.01); *A61K 31/16* (2013.01); *A61K 31/201* (2013.01); *A61K 31/202* (2013.01); *A61K 31/203* (2013.01); *A61K 31/215* (2013.01); *A61K 31/557* (2013.01); *A61K 31/5575* (2013.01); *A61K 31/661* (2013.01); *A61K 31/683* (2013.01); *A61K 9/08* (2013.01)

(58) Field of Classification Search
None
See application file for complete search history.

(56) References Cited

U.S. PATENT DOCUMENTS

| | | |
|---|---|---|
| 3,577,446 A | 5/1971 | Rakhit |
| 4,330,383 A | 5/1982 | Ellis et al. |
| 4,495,313 A | 1/1985 | Larsen |
| 4,889,664 A | 12/1989 | Kindt-Larsen et al. |
| 4,915,974 A | 4/1990 | D'Amelia et al. |
| 5,032,392 A | 7/1991 | Varma |
| 5,039,459 A | 8/1991 | Kindt-Larsen et al. |
| 5,337,888 A | 8/1994 | Morrison |
| 5,434,183 A | 7/1995 | Larsson-Backstrom |
| 5,460,802 A | 10/1995 | Asami et al. |
| 5,472,703 A | 12/1995 | Vanderlaan et al. |
| 5,656,667 A | 8/1997 | Breivik et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,849,811 A | 12/1998 | Nicolson et al. |
| 5,965,631 A | 10/1999 | Nicolson et al. |
| 5,998,498 A | 12/1999 | Vanderlaan et al. |
| 6,087,415 A | 7/2000 | Vanderlaan et al. |
| 6,531,432 B2 | 3/2003 | Molock et al. |
| 6,645,978 B1 | 11/2003 | Gamache et al. |
| 7,378,444 B2 | 5/2008 | Goodman et al. |
| 7,553,860 B2 | 6/2009 | Nicolson et al. |

(Continued)

FOREIGN PATENT DOCUMENTS

| | | |
|---|---|---|
| JP | 63-246331 | 10/1988 |
| JP | 2000107277 | 5/1994 |

(Continued)

OTHER PUBLICATIONS

Extended European Search Report—Appln. No. 19178469.3-1112 dated Sep. 10, 2019.
Arachidonic acid, Sigma-Aldrich Product Information, 2016.
Burri et al, Marine Omega-3 Phospholipids: Metabolism and Biological Activities, International Journal of Molecular Sciences, vol. 13, pp. 15401-15419, 2012.
Christie, Resolvins and protectins: chemistry and biology (lipidlibrary.aocs.org) 2010.
Cis-4, 7, 10, 13, 16, 19-Docosahexaenoic acid Product Info, Sigma-Aldrich, 2016.
Contact Lens Spectrum (Jul. 2010).

(Continued)

*Primary Examiner* — Craig D Ricci

(57) ABSTRACT

The present invention relates to ophthalmic compositions and methods for the treatment of dry eye and other inflammatory ocular conditions. In particular, the present invention relates to a composition comprising an esterified anti-inflammatory lipid mediator, which is an ester of an anti-inflammatory lipid mediator that is a reaction product of the anti-inflammatory lipid mediator and a monohydric alcohol or an amide wherein the majority of the anti-inflammatory lipid mediator is present in an ester form. In this way, the compositions are substantially free of an acid form of the anti-inflammatory lipid mediators. This composition can be topically delivered to the ocular surface via a preparation, solution, gel, ointment, and/or strip and/or a contact lens.

12 Claims, No Drawings

(56) References Cited

U.S. PATENT DOCUMENTS

| | | | |
|---|---|---|---|
| 7,884,141 | B2 | 2/2011 | Salamone et al. |
| 2002/0095000 | A1 | 7/2002 | Troyer et al. |
| 2002/0137793 | A1 | 9/2002 | Klimko |
| 2004/0210065 | A1 | 10/2004 | Miron et al. |
| 2005/0054723 | A1 | 3/2005 | Stjernschantz |
| 2005/0115697 | A1 | 6/2005 | Dueppen et al. |
| 2005/0220742 | A1 | 10/2005 | Breen |
| 2006/0251685 | A1 | 11/2006 | Yu et al. |
| 2007/0265341 | A1 | 11/2007 | Dana et al. |
| 2007/0293410 | A1 | 12/2007 | Surowiak |
| 2008/0161275 | A1 | 7/2008 | Gjorstrup |
| 2010/0048847 | A1 | 2/2010 | Broad |
| 2010/0105771 | A1 | 4/2010 | de Long et al. |
| 2010/0105772 | A1 | 4/2010 | Serhan et al. |
| 2010/0105773 | A1 | 4/2010 | Smith et al. |
| 2010/0140114 | A1 | 6/2010 | Pruitt et al. |
| 2010/0305045 | A1 | 12/2010 | Yu |
| 2011/0223269 | A1 | 9/2011 | Okamoto |

FOREIGN PATENT DOCUMENTS

| | | |
|---|---|---|
| JP | 200010055 | 1/2000 |
| JP | 6123860 | 4/2000 |
| JP | 2001 188204 A | 7/2001 |
| RU | 2172169 02 | 8/2001 |
| RU | 2336851 C1 | 2/2017 |
| WO | 1996029984 A1 | 10/1996 |
| WO | 1999027978 A1 | 6/1999 |
| WO | 1999029750 A1 | 6/1999 |
| WO | 1999040906 A2 | 8/1999 |
| WO | 2000021528 A1 | 4/2000 |
| WO | 2000022459 A1 | 4/2000 |
| WO | 2000022460 A1 | 4/2000 |
| WO | 2000026698 A1 | 5/2000 |
| WO | 2001055083 A1 | 8/2001 |
| WO | WO 02/02105 A1 | 1/2002 |
| WO | 2003/022321 A2 | 3/2003 |
| WO | 2004006801 A2 | 1/2004 |
| WO | 2006007510 A1 | 1/2006 |
| WO | 2008058274 A2 | 5/2008 |
| WO | 2008061992 A2 | 5/2008 |
| WO | 2009025763 A2 | 2/2009 |
| WO | 2009032132 A1 | 3/2009 |
| WO | 2009051670 A2 | 4/2009 |
| WO | 2010106571 A2 | 9/2010 |
| WO | WO 2010/103404 A1 | 9/2010 |
| WO | 2004004738 A1 | 1/2014 |

OTHER PUBLICATIONS

Fekrat et al, The effect of oral 13-cis-retinoic acid on retinal redetachment after surgical repair in the eyes with proliferative vitreoretinopathy, Ophthalmology, Mar. 1995, 102 (3): 412-8.
Hertrampf, et al., "Handbook on ingredients for Aquaculture Feeds", Springer-Science+Business Media, B.V., 2000, Abstract.
Heryanto, et al., "Solubility of Stearic Acid in Various Organic Solvents and Its Prediction using Non-ideal Solution Models", Science Asia 33, 2007, 469-472.
Human_Metabolome_Database, 2011, http://www.hmdb.ca/metabolites/HMDB12587.
International Preliminary Report on Patentability, dated Jan. 14, 2014, for PCT Int'l Appln. No. PCT/US2012/043078.
International Preliminary Report on Patentability, dated Jan. 14, 2014, for PCT Int'l Appln. No. PCT/US2012/043079.
Internet Archive Report of www.systane.com available online as of Oct. 13, 2009.
Khanal, et al., "Nanoscale phase dynamics of the normal tear film", Nanomedicine: Nanotechnology, Biology, and Medicine vol. 6, 2010, pp. 707-713.
King, 2012: http://themedicalbiochemistrypage.org/eicosanods.html.
Linoleic acid, Sigma-Aldrich Product Information, 2016.
Longqin Hu, Edited by Binghe Wang, et al: "Drug Delivery: 8. Prodrug Approaches to Drug Delivery", Drug Delivery: Principles and Applications, Hoboken, N.J.: Wiley-Interscience, pp. 125-265, May 13, 2005, XP002523674, ISBN: 978-0-471-47489-0 Retrieved from the Internet: URL:http://www3.interscience.wiley.com/dgi-bin/summary/110494622/SUMMARY.
Matsukawa, et al., "Molecular Diffusion in Polysaccharide Gel Systems as Observes by NME", Progr Colloid Polym Sci, vol. 136, 2009, pp. 171-176.
Mikawa et al, Ocular Activity of Topically Administered Anandamide in the Rabbit, Jpn J Ophthalmol 41, 217-220, 1997.
Nguyen, et al., "Three-Dimensional Construct of the Human Corneal Epithelium for In Vitro Toxicology", Journal of Applied Toxicology, in press, 2002, to be released In: Alternatives Toxicological Methods. Boca Raton, FL, CRC Press ed Katz SA and Salem H, 2003. Chapter 14: p, 147-159.
Ophardt, 2003: http://www.elmhurst.edu/~chm/vchembook/555prostagland.html.
Opstvedt, "Fish Lipids in Animal Nutrition", informa Technical Bulletin, No. 22, Oct. 1985, 29 pgs.
Patel, et al., "Chemical and physical analyses of wax ester properties", 7 pp., Journal of Insect Science, 1.4., 2001. Available online: insectscience.org.
PCT International Search Report, dated Aug. 22, 2012, for PCT Int'l Appln. No. PCTUS2012043079.
PCT International Search Report, dated Aug. 27, 2012, for PCT Int'l Appln. No. PCT/US2012/043078.
Plewig, et al., "Anti-inflammatory effects of 13-Cis-retinoic acid. An in vivo study.", Archives of Dermatological Research, 1981, vol. 270, No. 1, pp. 89-94, Abstract Only.
Rashid et al, Topical Omega-3 and Omega-6 Fatty Acids for Treatment of Dry Eye, Archives of Ophthalmology, 2008, 219-225, 126(2), US,
St. Edwards University website, Structure/Overview: Leukotrienes and Lipoxins, http://www.cs.stedwards.edu/chem/Chemistry/CHEM43/CHEM43/Leukotr/STRUCTURE.HTML.
Wermuth, et al, The Practice of Medicinal Chemistry, Designing Prodrugs and Bioprecursors I: Carrier Prodrugs, 1996, pp. 672-696, vol. 31, Academic Press Limited.
www.systane.com (disclosing Systane Contacts Lubricant Eyes Drops—available online as of Oct. 13, 2009).
Merriam-Webster Online Dictionary (available at https://www.merriam-webster.com/dictionary/associate; accessed Mar. 7, 2019) Year 2019. (in corresponding U.S. Appl. No. 14/366,137—Office Action dated Mar. 14, 2019).

ESTERS FOR TREATMENT OF OCULAR INFLAMMATORY CONDITIONS

RELATED APPLICATIONS

This application is a continuation of U.S. patent application Ser. No. 13/495,049, filed on Jun. 13, 2012, which claims priority to U.S. Provisional Patent Application Ser. No. 61/503,158, filed on Jun. 30, 2011.

TECHNICAL FIELD

The present invention relates to ocular products containing esterified anti-inflammatory lipid mediators for relief of dry eye or treatment of inflammatory ocular conditions. Provided is an ophthalmic composition that comprises an esterified anti-inflammatory lipid mediator. Further provided are sterile preparations, solutions, gels, ointments, and/or strips for administration to the eye and/or a contact lens that comprises an esterified anti-inflammatory lipid mediator.

BACKGROUND

It is known that sufficient lubrication is necessary for good eye health. Tears nourish the ocular tissues and protect the surface of the eye from foreign bodies. Changes in the ocular surface due to alterations in the quality or quantity of tears (caused by either decreased tear production or increased tear film evaporation) can lead to dry eye syndrome and other inflammatory ocular conditions. Typical symptoms of dry eye and other inflammatory ocular conditions include dryness, burning, itchiness, scratchiness, stinging, a sandy/gritty sensation, tired eyes, and sensitivity to light. These symptoms typically worsen as the day progresses. Other symptoms include pain, redness, a pulling sensation, pressure behind the eye, and a feeling that there is something in the eye. Because of the range of symptoms, individuals suffering from dry eye and other inflammatory ocular conditions often complain of eye irritation and discomfort.

If dry eye and other inflammatory ocular conditions are left untreated, it can produce complications that can cause eye damage, resulting in impaired vision or (rarely) the loss of vision. When symptoms are severe, they can interfere with the quality of life of an individual suffering from dry eye.

The ocular surface is normally covered by a tear film—the clear liquid that coats the outer tissues of the eye. The tear film is composed of three layers; the most superficial layer of the tear film is the lipid layer, which covers the aqueous layer of the tear film, and then the third layer is a mucinous layer. Any abnormality in any one of the three layers, particularly a disturbance in the lipid layer, produces an unstable tear film, which results in symptoms of dry eye and other inflammatory ocular conditions.

Current methods of alleviating the symptoms of dry eye include administering artificial tears to the ocular surface. These artificial tears, however, must be administered every few hours, and only provide temporary and incomplete relief of the symptoms of dry eye. Thus, there is a need for compositions and methods to treat various eye disorders and conditions, including but not limited to, dry eye syndrome and other inflammatory ocular conditions.

It has been noted that consumption of dark fleshed fish containing dietary omega-three fatty acids is associated with a decreased incidence of dry eye symptoms. Omega-three and omega-six fatty acids are compounds known as "essential" fatty acids because they are essential to human health. These fatty acids, however, are not produced by the human body; instead, the fatty acids can be introduced into the body via dietary intake, either in the form of food or as supplements. Oral consumption of omega-three fatty acids, however, does produce potential side effects such as effects on bleeding time, increasing cholesterol (LDL) level, high caloric intake, a fishy aftertaste, and gastrointestinal disturbances. Because of their potential to improve the symptoms of dry eye and other inflammatory ocular conditions, work on omega-three fatty acids when used in a topical application to the ocular surface has shown promising results. (Rashid, S. et al., "Topical Omega-3 and Omega-6 Fatty Acids for Treatment of Dry Eye," Arch Opthalmol. 2008; 126(2):219-225). Using topical formulations of fatty acids to treat dry eye would provide more flexibility for treatment, including lessening side-effects that patients can experience from oral intake of fatty acids.

Omega-three fatty acid-containing oils such as botanical oils have been used to form non-irritating ophthalmic compositions (e.g., U.S. Patent Application Pub. 2010/0305045 (Abbott Medical Optics, Inc.)). Hydrogel contact lenses can comprise a polymeric matrix and a hydrophobic comfort agent distributed in the polymeric matrix, where the hydrophobic comfort agent can include a monoglyceride, a diglyceride, a triglyceride, a glycolipid, a glyceroglycolipid, a sphingolipid, a sphingoglycolipid, a phospholipid, a fatty acid, a fatty alcohol, a hydrocarbon having a $C_{12}$-$C_{28}$ chain in length, a mineral oil, a silicone oil, or a mixture thereof. (U.S. Patent Application Pub. 2010/0140114 (Ciba Vision Corporation)). Ophthalmic lenses have been provided with anti-toxin agents that are monoesters and/or diesters of a polyhydric aliphatic alcohol and a fatty acid containing from eight to eighteen carbon atoms and wherein said monoester has at least one hydroxyl group associated with its aliphatic alcohol residue (U.S. Pat. No. 5,472,703). Resolvins and protectins have been used to help treat pathologies associated with angiogenesis and ocular neovascularization, particularly associated with retinopathy of prematurity (e.g., U.S. Patent Application Pub. 20100105773 (Children's Medical Center Corp.)). Lipoxins have also been used to treat pathologies associated with ocular neovascularization (e.g., U.S. Patent Application Pub. 20100105772 (Serhan, et. al.)).

Accordingly, there remains a need in the art for improved ocular products that relieve/mediate symptoms of dry eye and other inflammatory ocular conditions.

SUMMARY

In one embodiment, the present invention provides an ophthalmic composition for treatment of ocular conditions, the composition comprising an ester or amide of an anti-inflammatory lipid mediator that is a reaction product of the anti-inflammatory lipid mediator and a monohydric alcohol or an amide. Generally, the majority of the anti-inflammatory lipid mediator is present in an ester form. This is in contrast to anti-inflammatory lipid mediators being present in an acid form. In one or more embodiments, the composition is substantially free of fatty acids. Such an esterified anti-inflammatory lipid mediator can be dispersible and/or dissolvable or emulsifiable in an aqueous delivery system.

In another embodiment, the present invention provides a sterile preparation, solution, gel, ointment, emulsion or strip for administration to the eye or a contact lens comprising an esterified anti-inflammatory lipid mediator.

In a further embodiment, the present invention provides a method of treating, preventing or mitigating inflammatory ocular conditions and/or dry-eye in an individual in need thereof which comprises delivering to such individual's ocular surface a therapeutically effective amount of a composition comprising an anti-inflammatory lipid mediator.

These and other embodiments of the invention will become apparent from the following description of the presently preferred embodiments. The detailed description is merely illustrative of the invention and does not limit the scope of the invention, which is defined by the claims and equivalents thereof. Variations and modifications of the invention may be effected without departing from the spirit and scope of the novel contents of the disclosure.

DETAILED DESCRIPTION

Provided are processes of making and using ocular products containing esterified anti-inflammatory lipid mediators, wherein the majority of the anti-inflammatory lipid mediator is present in an ester form. It has been discovered that the use of esterified anti-inflammatory lipid mediators, when the majority of the anti-inflammatory lipid mediator is present in the ester form, results in an ocular product that greatly improves initial comfort upon contact with or administration to the ocular surface. Ocular products include, but are not limited to, preparations, solutions, gels, ointments, emulsions, strips, ophthalmic devices, and the like any which can be administered to the ocular surface, including the eye.

With respect to terms used in this disclosure, the following definitions are provided.

Reference to "anti-inflammatory lipid mediator" includes those molecules that play a role (directly or indirectly) in the inhibition of cytokine production by epithelial cells or immune cells, in the inhibition of reactive oxygen species (ROS) production by epithelial cells or immune cells, in the control and/or inhibition of recruitment of white blood cells (reduction in leukocytes infiltration), and/or in the resolution of inflammation (promotion of uptake of dead cells). Suitable anti-inflammatory lipid mediators are generally acid-based entities whose carboxylic groups of the hydrocarbon chain can be esterified. The majority of the anti-inflammatory lipid mediator is present in the ester form. Anti-inflammatory lipid mediators can be reacted with hydroxyl groups of various entities as desired. The hydroxyl groups are delivered by monohydric alcohols that can provide therapeutic benefits to the eye, including osmoprotection, in conjunction with the esterified anti-inflammatory lipid mediators.

As used herein, the term "about" refers to a range of +/−5% of the number that is being modified. For example, the phrase "about 10" would include both 9.5 and 10.5.

As used herein, the use of "a," "an," and "the" includes the singular and plural.

As used herein, the term "ophthalmic composition" refers to a compound or mixture suitable for administration to the eye or ocular surface. Ocular compositions include preparations, solutions, gels, ointments, emulsions, strips and the like.

As used herein the term "sterile preparation" includes any compound or mixture for direct administration to any part of a mammalian body, including implantation, injection, administration as a drop, gel or wash, and the like, wherein the preparation is substantially free from undesired foreign matter just prior to administration. Methods for insuring sterility include aseptic packaging and sterilization by exposure to radiation, heat combinations thereof and the like.

As used herein, the term "individual" includes humans and vertebrates.

As used herein, the term "agent" includes any compound, composition, to be tested for efficacy in the methods disclosed herein.

As used herein the term "ocular surface" includes the wet-surfaced and glandular epithelia of the cornea, conjunctiva, lacrimal gland, accessory lacrimal glands, nasolacrimal duct and meibomian gland, and their apical and basal matrices, puncta and adjacent or related structures, including the eyelids linked as a functional system by both continuity of epithelia, by innervation, and the endocrine and immune systems.

As used herein, the term "contact lens" refers to a structure that can be placed on the cornea of an individual's eye. The contact lens may provide corrective, cosmetic, therapeutic benefit, including wound healing, delivery of drugs or neutraceuticals, diagnostic evaluation or monitoring, or UV blocking and visible light or glare reduction, or a combination thereof. A contact lens can be of any appropriate material known in the art, and can be a soft lens, a hard lens, or a hybrid lens.

As used herein, the term "silicone hydrogel contact lens" refers to a contact lens formed from a polymer comprising silicone containing and hydrophilic repeating units.

As used herein, the term "hydrogel" or "hydrogel material" refers to a hydrated crosslinked polymeric system that contains water in an equilibrium state. Hydrogels generally contain at least about 15 wt % water, and in some embodiments at least about 20 wt % water at equilibrium.

Conventional hydrogels are prepared from monomeric mixtures predominantly containing hydrophilic monomers, such as 2-hydroxyethyl methacrylate ("HEMA"), N-vinyl pyrrolidone ("NVP"), or vinyl acetate. U.S. Pat. Nos. 4,495,313, 4,889,664, and 5,039459 disclose the formation of conventional hydrogels.

As used herein, the term "silicone hydrogel" refers to a hydrogel obtained by copolymerization of at least one silicone-containing monomer, macromer, prepolymer, with at least one hydrophilic component. Examples of silicone hydrogels include balafilcon, acquafilcon, lotrafilcon, comfilcon, galyfilcon, senofilcon, narafilcon, falcon II 3, asmofilcon A, as well as silicone hydrogels as prepared in U.S. Pat. No. 5,998,498, WO 03/22321, U.S. Pat. Nos. 6,087,415, 5,760,100, 5,776,999, 5,789,461, 5,849,811, 5,965,631. U.S. Pat. No. 7,553,880, WO 2008/061992, and U.S. 2010/048847. These patents, as well as all other patents disclosed in this paragraph, are hereby incorporated by reference in their entireties.

Hard contact lenses are made from polymers that include but are not limited to polymers of poly(methyl)methacrylate, silicon acrylates, fluoroacrylates, fluoroethers, polyacetylenes, and polyimides, where the preparation of representative examples may be found in JP 200010055, JP 6123860 and U.S. Pat. No. 4,330,383. Intraocular lenses of the invention can be formed using known materials. For example, the lenses may be made from a rigid material including, without limitation, polymethyl methacrylate, polystyrene, polycarbonate, or the like, and combinations thereof. Additionally, flexible materials may be used including, without limitation, hydrogels, silicone materials, acrylic materials, fluorocarbon materials and the like, or combinations thereof. Typical intraocular lenses are described in WO 0026698, WO 0022460, WO 9929750, WO 9927978, WO 0022459, and JP 2000107277. All of the references mentioned in this application are hereby incorporated by reference in their entireties.

A therapeutically effective amount of an anti-inflammatory lipid mediator is an amount effective to produce a clinically recognizable favorable change in the pathology of the disease or condition being treated. A therapeutically effective amount includes those effective to treat, reduce, alleviate, ameliorate, mitigate, eliminate or prevent one or more symptoms of the ocular conditions sought to be treated or the condition sought to be avoided or treated.

One of skill in the art would readily be able to determine what is a therapeutically effective amount or an effective amount.

As used herein, the term "inflammatory ocular condition" includes dry eye syndromes, which is also called keratoconjunctivitissicca (KCS). Dry eye is a multifactorial disease of the tears and ocular surface that results in symptoms of discomfort, visual disturbance, and tear film instability with potential damage to the ocular surface. It is accompanied by increased osmolarity of the tear film and inflammation of the ocular surface. Dry Eye Syndrome (DES) is defined as a disorder of the tear film, resulting from tear deficiency and/or excessive tear evaporation, causing damage to the ocular surface and causing symptoms of ocular discomfort. There are two main forms of dry eye syndrome: tear deficiency forms (including Sjögren's syndrome and non-Sjögren's tear deficient) and evaporative forms. The tear film normally covers the front part of the eye, namely the cornea and the conjunctiva. The tear film is constantly exposed to multiple environmental factors, including variable temperature, airflow, and humidity, which may stimulate or retard its evaporation. In particular, a low humidity setting in the presence of a significant airflow increases the tear evaporation rate, as is frequently reported by subjects in desiccating environments. Indeed, even people with a normal tear secretion rate may experience dry eye symptoms while exposed to dry environments, such as in airplanes and dry workplaces.

Dry eye can also be defined as a condition with a decrease or change in quality of tears irrespective of the presence or absence of corneal and conjunctival lesions. It includes dry eye conditions found in individuals who have hypolacrimation, alacrima, xerophthalmia, and diabetes, HIV/AIDS etc.; post-cataract surgery dry eye; allergic conjunctivitis-associated dry eye; dry-eye associated with prolonged contact lens use; and age-related dry-eye syndrome. Dry eye can also include the conditions found in hypolacrimation individuals induced by long time visual display terminal (VDT) operations, room dryness due to air-conditioning, and the like. An "inflammatory ocular condition" can also refer to, but is not limited to: keratoconjunctivitissicca (KCS), age-related dry eye, Stevens-Johnson syndrome, Sjögren's syndrome, ocular cicatricalpemphigoid, blepharitis, corneal injury, infection, Riley-Day syndrome, congenital alacrima, nutritional disorders or deficiencies (including vitamin), pharmacologic side effects, eye stress, glandular and tissue destruction, environmental exposure (e.g. smog, smoke, excessively dry air, airborne particulates), autoimmune and other immunodeficient disorders, and comatose individuals rendered unable to blink.

As used herein "contact lens related dry eye" ("CLRDE") is a disorder marked by at least one objective clinical symptom and at least one subjective symptom. Clinical symptoms are selected from (a) a tear film break up time ("TFBUT") of less than about 10 seconds in at least one eye; (b) a fluorescein staining score ≥3 on a scale of 0-15 in at least one eye; (c) a lissamine green staining score ≥3 on a scale of 0-18 in at least one eye; or (d) a tear meniscus grade of 'abnormal' in at least one eye. Subjective symptoms are determined via patient feedback and include (a) ≥about 2 hour difference between average daily contact lens wear time and average daily comfortable contact lens wear time and (b) a rating of frequent or constant feelings of dryness, burning, stinging or discomfort during lens wear. CLRDE sign includes both excessive tear evaporation and Non-Sjogren's aqueous tear deficiency. Excessive tear evaporation is a disorder marked by a TFBUT of about 10 seconds or less in at least one eye or a TFBUT of 10 seconds or less in at least one eye as well as conjunctival or corneal staining of about 3 or greater on the NEI scale. Non-Sjogren's aqueous tear deficiency tear meniscus is a disorder marked by a grade of 'abnormal' in at least one eye or a tear meniscus grade of 'abnormal' in at least one eye as well as conjunctival or corneal staining of 3 or greater on the NEI scale.

As used herein the term "adnexal inflammation" includes inflammation of any area or part of the eye or ocular system, including but not limited to the eyelids, the lacrimal glands and extraocular muscles.

As used herein, there term "osmoprotection" means to maintain an ophthalmic osmolarity within a normal physiological range (preferably 270-320 mOsm/kg, with an average of about 290 mOsm/kg) and/or protect epithelial tissue against the effects of hypertonic conditions, where the unit "mOsm/kg" is milli-osmole per kilogram. Osmoprotectants, agents that offer osmoprotection, are generally uncharged, can be held within an ocular cell, are of relatively small molecular weight, and are otherwise compatible with cell metabolism. Osmoprotectants protect against hypertonicity below the ocular surface and provide hydration to the epithelial surface. Osmoprotectants include, without limitation, glycerol, inositol, sorbitol, xylitol, and erythritol.

As used herein, the term "unsaturated fatty acid" refers to a fatty acid containing at least one double or triple bond. Fatty acids in this class use the Greek alphabet to identify the location of double bonds. The "alpha" carbon is the carbon closest to the carboxyl group and the "omega" carbon is the last carbon of the chain. For example, linoleic acid, and gamma-linolenic acid (LA and GLA respectively) are omega-six fatty acids, because they have double bonds six carbons away from the omega carbon. Alpha-linolenic acid is an omega-three fatty acid because it has a double bond three carbon atoms from the omega carbon.

As used herein, the term "omega-three fatty acid" refers to fatty acids that have double bonds three carbon atoms from their omega carbon atom. For example, an omega-three fatty acid includes, but is not limited to alpha linolenic acid (ALA). Other omega-three fatty acids include derivatives of ALA. A "derivative" of ALA is a fatty acid that is made by a chemical modification performed upon alpha linolenic acid by, for example, an enzyme or is done by organic synthesis. Examples of omega-three fatty acids that are derivatives of ALA, include but are not limited to, eicosapentaenoic acid (EPA), docosahexaenoic acid (DHA), and the like. An "omega-three fatty acid" can comprise one or more omega-three fatty acids.

As used herein, the term "omega-six fatty acid" refers to one or more fatty acids that have a double bond 6 carbon atoms from their omega carbon atoms. For example, an omega-six fatty acid includes, but is not limited to linoleic acid (LA). Other omega-six fatty acids include derivatives of linolenic acid. A "derivative" of linoleic acid is a fatty acid that is made by a chemical modification performed upon linoleic acid. Examples of omega-six fatty acids that are derivatives of linoleic acid include, but are not limited to, gamma linolenic acid (GLA), dihomogammalinolenic acid (DGLA), and the like. In some embodiments, the composition comprises at least one non-inflammatory omega-six fatty acid. A non-inflammatory omega-six fatty acid is an omega-six fatty acid that does not promote or cause inflammation. In some embodiments the inflammation is in the eye or affects the ocular surface. One of skill in the art can determine if a fatty acid causes or promotes inflammation. If the fatty acid causes or promotes inflammation, the fatty acid can be excluded from the composition.

As used herein the term "linoleic acid" refers to 9,12-octadecandienoic acid, which has a short hand designation of 18:2(n-6), which is number of carbons:number double bonds (position). Throughout the specification linoleic acid is referred to as either linoleic acid or "LA".

As used herein the term "arachidonic acid" refers to 5, 8, 11, 14 eicosatetraenoic acid, which has a short hand designation of 20:4(n-6) and a molecular weight of 304.5. Throughout the specification arachidonic acid is referred to as either arachidonic acid or "AA". It should be noted that arachidonic acid can yield pro-inflammatory prostaglandins. It also should be noted that arachidonic acid can be involved in enzymatic processes that result in beneficial anti-inflammatory lipid mediators such as lipoxins and an endocannabinoid that is anandamide (arachidonoylethanolamine).

As used herein the term "alpha-linolenic acid" refers to 9, 12, 15 octadecatrienoic acid, which has a short hand designation of 18:3(n-3) and a molecular weight of 278.4. Throughout the specification alpha-linolenic acid is referred to as either alpha-linolenic acid or "ALA".

As used herein the term "gamma-linolenic acid" refers to 9, 6, 12,-octadecatrienoic acid, which has a short hand designation of 18:3(n-6) and a molecular weight of 278.4. Throughout the specification gamma-linolenic acid is referred to as either gamma-linolenic acid or "GLA".

As used herein the term "dihomogamma-linolenic acid" refers to 8, 11, 14 eicosatrienoic acid, which has a short hand designation of 20:3(n-6) and a molecular weight of 306.5. Throughout the specification eicosatrienoic acid is referred to as either eicosatrienoic acid or "DGLA".

As used herein the term "eicosapentaenoic acid" refers to 5,8,11,14,17-eicosapentaenoic acid, which has a short hand designation of 20:5(n-3) and a molecular weight of 302.5. Throughout the specification eicosapentaenoic acid is referred to as either eicosapentaenoic acid or "EPA".

As used herein the term "docosahexaenoic acid" refers to 4,7,10,13,16,19-docosahexaenoic acid, which has a short hand designation of 22:6(n-3) and a molecular weight of 328.6. Throughout the specification docosahexaenoic acid is referred to as either docosahexaenoic acid or "DHA".

As used herein, the term "ester" refers to any chemical compound derived by reaction of an oxoacid (an organic acid that contains oxygen) with a hydroxyl compound, such as an alcohol. Esters are usually derived from an organic acid in which at least one hydroxyl (—OH) group is replaced by an —O-alkyl (alkoxy) group. Most commonly, esters are formed by condensing a carboxylic acid with an alcohol. In one or more embodiments, the esters of the present invention can be naturally occurring, or can be formed by reaction of a fatty acid with an alcohol.

As used herein, the term "amidoester" refers to any chemical compound derived by reaction of an oxoacid with an amine. One or more embodiments provide that the reaction of a fatty acid with an amine provides an amidoester. Reference to the "ester form" can include the amidoester in addition to the traditional ester. Reference to "reaction product" means a resulting ester or amidoester that is formed by reaction of an acid with an alcohol or amine, regardless of whether the ester or amidoester is naturally-occurring or synthesized. If synthesized, the ester or amidoester can be prepared by various esterification methods known to one skilled in the art.

As used herein, the term "wax ester" refers to an ester of a fatty acid and a long-chain alcohol. Wax esters include, without limitation, beeswax and carnauba wax. Beeswax consists of $C_{40}$ to $C_{46}$ molecular species. Carnauba wax constitutes from $C_{16}$ to $C_{20}$ fatty acids esterified with $C_{30}$ to $C_{34}$ long-chain alcohols to provide a $C_{46}$ to $C_{54}$ molecular species.

As used herein, the term "alcohol" refers to any organic compound containing at least one hydroxyl functional group (—OH) bound to a carbon atom, that is usually bound to other carbon and hydrogen atoms; this includes, but is not limited to, acyclic alcohols; cyclic alcohols; primary, secondary, and tertiary alcohols; monohydric alcohols. The alcohols include monohydric alcohols, which are alcohols containing a single hydroxyl functional group. Monohydric alcohols include any compound of the formula $CH_3$—$(CH_2)_z$—OH wherein z is from 0 to 5, and in some embodiments 0-2. Monohydric alcohols can especially include ethanol, $CH_3$—$CH_2$—OH.

As used herein, the term "resolvin" is an agent that is generated from the interaction between an omega-three polyunsaturated fatty acid such as eicosapentaenoic acid (EPA) or docosahexaenoic acid (DHA), cyclooxygenase-II (COX-2) and an analgesic, such as aspirin. Resolvins of the E series are derived from EPA, whereas resolvins of the D series are derived from DHA. Exemplary resolvins include resolvin E1 (RvE1), resolvin E2 (RvE2), resolvin D1 (RvD1), resolvin D2 (RvD2), resolvin D3 (RvD3), resolvin D4 (RvD4), and combinations thereof.

As used herein, the term "protectin" or "neuroprotectin" is an agent, more particularly, a docosanoid (which is a signaling molecule made by oxygenation of 22-carbon essential fatty acids, especially DHA), that is derived from the polyunsaturated fatty acid docosahexaenoic acid (DHA). A "protectin" or "neuroprotectin" exerts potent anti-inflammatory and anti-apoptotic bioactivity at nanomolar concentrations in a variety of experimental models of brain and retinal diseases. An exemplary protectin includes protectin D1 (PD1).

As used herein, the term "lipoxin" refers to a series of anti-inflammatory lipid mediators that are synthesized by the 5-lipoxygenase pathway. Lipoxins are short-lived, endogenously produced, non-classic tetraene-containing eicosanoids, whose appearance in inflammation signals the resolution of inflammation. Lipoxins are also derived enzymatically from arachidonic acid, an omega-six fatty acid. Exemplary lipoxins include lipoxin A4 (LXA), lipoxin B4 (LXB4), and combinations thereof.

As used herein, the term "prostaglandin" refers to one of a number of hormone-like substances that participate in a wide range of body functions such as the contraction and relaxation of smooth muscle, the dilation and constriction of blood vessels, control of blood pressure, and modulation of inflammation. Prostaglandins are derived from omega-three and omega-six fatty acids acid. There are three main types of prostaglandins: Prostaglandin E1 (PGE1) and prostaglandin E3 (PGE3), which have anti-inflammatory properties, and prostaglandin E2 (PGE2), which promotes inflammation. PGE1, derived from dihomo-gamma-linolenic acid, is a potent vasodilator agent that increases peripheral blood flow, inhibits platelet aggregation, and has many other biological effects such as bronchodilation, and mediation of inflammation. PGE1 is important for lacrimal and salivary gland secretion and for T cell function. PGE2, derived from arachidonic acid, is released by blood vessel walls in response to infection or inflammation and acts on the brain to induce fever; PGE2 has also been used extensively as an oxytocic agent. PGE3, is formed via the cyclooxygenase (COX) metabolism of eicosapentaenoic acid. It is known that PGE3 lowers intraocular pressure.

As used herein, the term "retinoic acid" refers to a metabolite of Vitamin A (retinol) that mediates the functions of Vitamin A required for growth and development. Retinoic acids have been shown to have strong anti-inflammatory properties, in addition to their function as sebostaticums. (see Plewig, G., et al., Archives of Dermatological Research, Vol. 270, No. 1, 89-94). Retinoic acids can include, without limitation, 13-cis-retinoic acid.

As used herein, the term "endocannabinoid" refers to a class of organic compounds found produced within the body that activate cannabinoid receptors. Endogenous cannabinoids ("endocannabinoids"), when present in tissues at elevated concentrations, provide anti-inflammatory and analgesic effects. Endocannabinoids serve as intercellular lipid messengers, signaling molecules that are released from one cell and activating the cannabinoid receptors present on other nearby cells; they use retrograde signaling. Endocannabinoids are lipophilic molecules that are not very soluble in water. Endocannabinoids can include, without limitation, anandamide (arachidonoylethanolamine) and 2-arachidonoylglycerol.

As used herein, the term "phospholipid" refers to any of various phosphorous-containing lipids that are composed mainly of fatty acids, a phosphate group, and a simple organic molecule such as choline. Preferably, the phospholipids contain residues of one or more fatty acids that are omega-3 fatty acids, along with, as desired, omega-6 fatty acids. Phospholipids are amphipathic in nature; that is, the polar end of a phospholipid is soluble in water (hydrophilic) and aqueous solutions, while, the fatty acid end is soluble in fats (hydrophobic). In an aqueous environment, phospholipids combine to form a two-layer structure (lipid bilayer) with the hydrophobic ends in the middle and the hydrophilic ends exposed to the aqueous environment. Such lipid bilayers are the structural basis of cell membranes.

As used herein, the term "metabolite" refers to a compound that is the product of metabolism. A metabolite is formed as part of the natural biochemical process of degrading and eliminating compounds.

As used herein, the term "metabolically stable analog" refers to a compound that is a structural derivative of a parent compound (sometimes differing from the parent compound by a single element), or is a compound with similar properties to the parent compound. The analog is not easily degraded, and, thus, is metabolically stable.

As used herein the term "CD11b+ infiltration" includes the increase in CD11b$^+$ cells present in the center and periphery of the cornea following dry eye induction.

As used herein the term "IL-1α or TNF-α expression" includes measuring RNA transcripts of IL-1α and TNF-α by quantitative real-time Polymerase Chain Reaction.

As used herein the term "inflammatory cytokines" includes, without limitation, IL-1α and TNF-α.

Turning to the details of the disclosure, provided are processes of making and using ocular products containing esterified anti-inflammatory lipid mediators, wherein the majority of the anti-inflammatory lipid mediator is present in an ester form. One or more embodiments provide that the compositions are substantially free of fatty acids. That is, in such embodiments, the ocular products contain 10% by weight or less (or 8%, or 6%, or 5%, or 4%, or 3%, or 2%, or even 1%) of the acid form of the anti-inflammatory lipid mediator. In a further embodiment, the ocular products contain 1% by weight or less (or 0.8%, or 0.6%, or 0.5%, or 0.4%, or 0.3%, or 0.2%, or even 0.1%, or 0.05%, or 0.025%, or 0.01%) of the acid form of the anti-inflammatory lipid mediator. The esterified anti-inflammatory lipid mediators are esters of an acid anti-inflammatory lipid mediator. The esters may be formed by reacting the anti-inflammatory lipid mediator with at least one monohydric alcohol or amine. Other embodiments allow for the ester to be formed from an amine. Desirable anti-inflammatory lipid mediators include omega-three and/or omega-six fatty acids, resolvins or a metabolically stable analog, protectins or a metabolically stable analog, lipoxins or a metabolically stable analog, prostaglandins or a metabolically stable analog, retinoic acids, endocannabinoids, and phospholipids. Inflammation is a component of dry eye. There is a need to deliver active candidates, known to mitigate inflammation, in forms that are not associated with initial discomfort (acute ocular discomfort) upon administration to the eye, while providing long-term benefits to the eye.

One or more embodiments provide that the ester is provided in a therapeutically effective amount. That is, the ester is present in an amount sufficient to provide a beneficial effect to the ocular area, including but not limited to the ocular surface, the back of the eye, tear formation and stability. A therapeutically effective amount of ester can deliver an appropriate amount of anti-inflammatory lipid mediator that imparts a benefit to the ocular environment.

In the free fatty acid formulations (for example, alphalinolenic acid emulsions) of the prior art (e.g., those compositions disclosed in U.S. Patent Application Pub. 20070265341 (Dana et al.)), discomfort upon instillation to the eye has been found. A change in the concentration of surfactants (mostly Tween-80, from 2.5% to 0.25%) or the use of additional surfactant(s) (such as the amphoteric monateric surfactant) did not result in improved comfort upon instillation. The current invention seeks to avoid or remedy the discomfort issue by making the essential fatty acid non-ionic, i.e., using the esterified counterpart of the molecule.

Anti-inflammatory lipid mediators, such as polyunsaturated fatty acids, resolvins or a metabolically stable analog, protectins or a metabolically stable analog, lipoxins or a metabolically stable analog, prostaglandins or a metabolically stable analog, retinoic acids, endocannabinoids, and phospholipids are desirable ingredients of ocular products for use in treating such ocular conditions as inflammation, dry eye and/or dryness symptoms, and meibomian gland dysfunction. It has been discovered that the use of esterified anti-inflammatory lipid mediators, when the majority of the anti-inflammatory lipid mediator is present in the ester form, results in an ocular product that greatly improves initial comfort upon contact with or administration to the ocular surface. Generally, the esterified anti-inflammatory lipid mediator is a reaction product of an acid anti-inflammatory lipid mediator and an alcohol or an amine.

Such esterified anti-inflammatory lipid mediators may also be useful in a rewetting drop, in some instances unpreserved, or may be associated with a contact lens, such as a silicone hydrogel, whereby the lens may be treated with a mixture of the esterified anti-inflammatory lipid mediators. The esterified anti-inflammatory lipid mediators can be incorporated into the contact lens using various methods, for example, incorporation can occur during the lens extraction or hydration process or a combination thereof.

Such a characteristic is not offered by previous uses of fatty acids and/or fatty acid oils. The esterified anti-inflammatory lipid mediators can be combined with an aqueous delivery system—for desired ophthalmic compositions.

Esterified anti-inflammatory lipid mediators, when the majority of the anti-inflammatory lipid mediator is present in the ester form, have the advantage of targeting the inflammatory component of the dry eye disease (which perpetuates dry eye disease) and are less likely to cause initial discomfort at a wider concentration range. Upon contact with and uptake to the cells of the ocular surface, and without intending to be bound by theory, it is thought that esterified anti-inflammatory lipid mediators, such as esterified polyunsaturated fatty acids, esterified resolvins or a metabolically stable analog, esterified protectins or a metabolically stable analog, esterified lipoxins or a metabolically stable analog, esterified prostaglandins or a metabolically stable analog, esterified retinoic acids, endocannabinoids, and phospholipids, undergo hydrolysis and return to their acidic anti-inflammatory lipid mediator state along with the alcohol that was used in forming the ester.

Turning to the esters of polyunsaturated fatty acids such as omega-three and omega-six fatty acids, the reaction of carboxylic acids and alcohols or acetates will produce esters. In general terms, the following fatty acid derivatives such as esters (Ia) and other functionalities such as amides (Ib) are desirable for their stability and improved initial eye comfort:

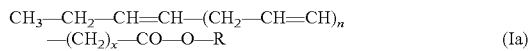
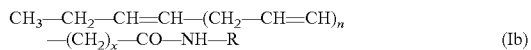
(Ia)

$CH_3$—$CH_2$—CH=CH—($CH_2$—CH=CH)$_n$
—($CH_2$)$_x$—CO—O—R $CH_3$—$CH_2$—CH=CH—($CH_2$—CH=CH)$_n$
—($CH_2$)$_x$—CO—NH—R (Ib)

Such derivatives are then expected to be converted back to their original fatty acid structure (II):

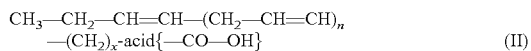

$CH_3$—$CH_2$—CH=CH—($CH_2$—CH=CH)$_n$
—($CH_2$)$_x$-acid{—CO—OH} (II)

Once in the ocular environment and/or incorporated into the lipid layer or cell membrane lipid bilayer to carry-on their tear film stabilization effect and/or anti-inflammatory effect.

The ranges of n, x and R can fall within the following ranges: n: 2-5; x: 2-7; R: ophthalmologically compatible leaving group included, but not limited to:

—($CH_2$)$_y$$CH_3$, where y is 0, 1 or above. In some embodiments y is between 0 and 5, or even 0 and 3, with y=1 being preferred.

Specifically, without limitation, the esterified anti-inflammatory lipid mediator comprises an esterified omega-three fatty acid, wherein the omega-three fatty acid is selected from the group consisting of: alpha-linolenic acid, stearidonic acid, eicosatetraenoic acid, eicosapentaenoic acid, docohexaenoic acid, docosapentaenoic acid (DPA), tetracosapentaenoic acid, and tetracosahexaenoic acid (Nisinic acid), derivatives, metabolites, and mixtures thereof. Upon esterification, the majority of the esterified anti-inflammatory lipid mediator is present in the ester form of the omega-three fatty acid.

Specially, esterified omega-three fatty acids can be selected from the following non-limiting examples: ethyl linolenate (alpha-linolenic acid ethyl ester (ALA-EE); stearidonic acid ethyl ester and stearidonic acid propyl ester; eicosatetraenoic acid ethyl ester and eicosatetraenoic acid propyl ester; eicosapentaenoic acid ethyl ester and eicosapentaenoic acid propyl ester; and docohexaenoic acid ethyl ester and docohexaenoic acid propyl ester.

The anti-inflammatory lipid mediator is reacted with a monohydric alcohol or an amine to form the desired ester form of the anti-inflammatory lipid mediator. Monohydric alcohols containing a single hydroxyl functional group. Suitable monohydric alcohols include up to 5 carbon atoms. In one embodiment, the monohydric alcohols have the formula $CH_3$—($CH_2$)$_z$—OH wherein z is 0 to 5. In another embodiment the monohydric alcohols are selected from methanol and ethanol. In another embodiment the monohydric alcohol is ethanol.

Suitable amines include primary and secondary amines having up to 6 carbon atoms. The amines may be linear, branched or cyclic. In one embodiment suitable amines include amines having the formula $CH_3$—($CH_2$)$_z$—$NH_2$ wherein z is 0 to 5, and preferably 0 or 1.

The inflammatory lipid mediator and monohydric alcohol are reacted under ester forming conditions. Suitable catalysts are known in the art and include acids, bases, carbodiimide, and the like. The esterification and amidation reactions can take place at room temperature (typically in the range of about 19-25° C.) without much need to go higher and ambient pressure, temperatures can be brought to higher ranges (about 25° C. to 80° C.) in order to accelerate the time to reaction completion.

It should be noted that an esterified anti-inflammatory lipid mediator does not take the form of naturally occurring oils including sunflower oil, sesame oil, castor oil, linseed oil, and the like. It should be further noted that the esterified anti-inflammatory lipid mediators of the present invention are not wax esters as they are formed from alcohols having short carbon chains (six or less and in some embodiments 3 or less carbon atoms).

Mixtures may include omega-three and omega-six fatty acid esters at desired ratios. In one or more embodiments it is desirable to provide a composition which will, upon hydrolysis of the ester, provide a balance of omega-three fatty acid:omega-six fatty acid in the eye to about 1:1. In other embodiments it is desirable to provide ophthalmic compositions which have ratios of the omega-three fatty acid:omega-six fatty acid upon hydrolysis, in the range of about 10:about 1 to no less than about 1:about 1 and from about 5:1 to about 1:1, from about 4:1 to about 1:1, from about 3:1 to about 1:1, from about 2:1 to about 1:1, about 1:1, about 2:1, about 3:1, about 4:1, about 5:1, about 6:1, about 7:1, about 8:1, about 9:1, or about 10:1. The ratio is based on the total amount of each class of omega fatty acids.

Mixing of the ophthalmic compositions can be done under aseptic conditions, or under ambient conditions and then sterilized. Temperature can range widely and the reactions may be performed under ambient conditions of temperature and pressure.

In addition to the usefulness of esterified anti-inflammatory lipid mediators as ingredients in ophthalmic compositions, including re-wetting drops, multipurpose solutions, cleaning and storing solutions and in contact lenses themselves, such materials are also candidates for their inclusion in lens packing solution. Lenses may be packaged with esterified anti-inflammatory lipid mediators in formulations and/or emulsions or may be hydrated in such materials as dissolved in appropriate solvent(s), followed by equilibration of the lens in packing solution.

Other ophthalmic compositions include lens care solutions such as multipurpose solutions, preparations, gels, ointments, emulsions, and ophthalmic products such as strips, inserts or punctal plugs or any product coming into contact with the ocular surface.

In one embodiment, the esterified anti-inflammatory lipid mediators are provided in an aqueous delivery system. Aqueous delivery systems are water based systems, which can be instilled directly in the eye, or may be used to condition, store, or clean ophthalmic devices which are placed in the ocular environment. Examples of aqueous delivery systems can include one or more of the following: packing solutions, storing solutions, cleaning and care solutions, multipurpose solutions, conditioning solution and ophthalmic drops. The aqueous delivery systems may also include known components, such as one or more of emulsifiers, chelant agents, or stabilizers, surfactants, wetting agents, antioxidants, tonicity adjusting agents, preservatives, osmoprotection agents, combinations thereof, and the like.

The packaging solution may be any water-based solution including that which is used for the storage of contact lenses. The esterified anti-inflammatory lipid mediators are dispersed in the packaging solution. Typical solutions include, without limitation, saline solutions, other buffered solutions, and deionized water. The preferred aqueous solution is saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (YMS), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, and the like and combinations thereof. Preferably, the solution is a borate buffered or phosphate buffered saline solution.

To form the packaging solution, at least one surfactant or emulsifier along with any additional ingredients are combined with the water-based solution, stirred, and dissolved or dispersed. The pH of the solution preferably is adjusted to about 6.2 to about 7.5. The lens to be stored in the packaging solution of the invention is immersed in the solution and the solution and lens placed in the package in which the lens is to be stored. Alternatively, the solution may be placed into the package and the lens then placed into the solution. Typically, the package is then sealed by any convenient method, such as by heat sealing, and undergoes a suitable sterilization procedure.

The surfactants suitable for use in the invention are of any suitable molecular weight, preferably about 200 to about 1,000,000, more preferably about 1000 to about 18,000. Useful surfactants have a hydrophile-lipophile balance ("HLB") of about 10 to about 30, preferably about 15 to about 25, more preferably about 15 to about 23.

Any of the known surfactants fitting the aforementioned criteria may be used provided that the surfactant is compatible, in terms of solubility, in the solution with which it is used. Thus, suitable surfactants include, without limitation, cationic, ionic, non-ionic surfactants, and combinations thereof. However, the use of a lens packaging solution containing cationic and ionic surfactants may cause eye irritation. Therefore, preferably the surfactant is a non-ionic surfactant.

Suitable non-ionic surfactants include, without limitation, polyethylene glycol esters of fatty acids, such as polysorbate 20, 60 or 80, all available as TWEEN® surfactants, alkanolamides, amine oxides, ethoxylated alcohols and acids, and surfactants having one or more poly(oxyalkylene) chains, such as poloxamine surfactants (a surface-active agent that removes lipid and environmental debris from the lenses; polyalkoxylated block polymers of ethylene diamine) or poloxamer surfactants (any of a series of nonionic surfactants of the polyoxypropylene-polyoxyethylene copolymer type, used as surfactants, emulsifiers, stabilizers, and food additives), and the like, and combinations thereof. Preferably, the surfactant is a polysorbate or poloxamer surfactant. Poloxamer surfactants are commercially available under the name PLURONIC200 that are polyoxyethylene-polyoxypropylene non-ionic surfactants having polyoxyethyl hydrophilic group ends that make up about 10 to about 80 percent by weight of the molecule. Although any of the PLURONIC® surfactants are preferred, particularly preferred for use in the invention is PLURONIC® 127, which is about 70 percent by weight ethylene oxide and has a molecular weight of about 12,000 to about 15,0000.

The surfactant may be combined with any known active and carrier components useful for lens packaging solution or for a rewetting drop. Suitable active ingredients for lens packaging solutions include, without limitation, antibacterial agents, anti-dryness agents, such as polyvinyl alcohol, polyvinylpyrrolidone, and dextran, tonicity agents, and the like, and combinations thereof.

Suitable wetting agents, along with viscosity enhancers include, without limitation: methyl gluceth-20 (sold under the trade name, for example, Glucam E20), carboxymethylcellulose, dextran 70, gelatin, hydroxymethylcellulose, hydroxypropyl methylcellulose, hydroxypropylethylcellulose, hydroxypropyl cellulose, methylcellulose, PEG, propylene glycol, polyvinyl alcohol (PVA), polyvinylpyrrolidone (PVP), Carbomer, polymethylvinylethermaleic anhydride, hyaluronic acid, xanthan gum, and polyacrylicacid.

Suitable antioxidants used in this invention include, without limitation, hindered phenols, catechols, tocopherols, carotenoids, hyaluronic acid, lutein, or any species that can scavenge free radicals. Antioxidants are molecular species that inhibit oxidative damage of other chemicals through redox chemical reactions. These reactions typically transfer electrons for a molecule species to an oxidant molecule. These can include free radicals, which can cause chain reactions. In simplest terms, antioxidants are reducing agents. Examples of antioxidants include, without limitation: Vitamin E, Vitamin C, beta carotene (which is converted to Vitamin A), and peroxidases, and other agents which can inhibit the formation of free radicals, e.g., chelants, EDTA, diethylene triamine pentaacetic acid (DTPA), N, N-bis[carboxymethyl]glycine (NTA), and the like.

In some embodiments, Vitamin E is added to a solution comprising the esterified anti inflammatory lipid mediator.

In another embodiment the composition of the present invention is incorporated into an ophthalmic device such as a contact lens or, more particularly, a silicone hydrogel contact lens. In this embodiment the esterified anti-inflammatory lipid mediators, wherein the majority of the anti-inflammatory lipid mediator is present in the ester form, may be incorporated into the lens in a number of ways, including but not limited to incorporating into the reaction mixture from which the lens is polymerized, contacting the lens with a solution comprising the esterified anti-inflammatory lipid mediators either before during or after packaging. For example the esterified anti-inflammatory lipid mediators may be included in the extraction, hydration or storage solution during the manufacture of the lens or may be included in a solution which is contacted with the contact lens by the lens wearer. In one embodiment the solution swells the lens, which allows for enhanced uptake of the esterified anti-inflammatory lipid mediators. In embodiments where the esterified anti-inflammatory lipid mediator is incorporated into the reaction mixture, the esterified anti-inflammatory lipid mediator may be added to the reaction mixture as a separate component, or may be pre-reacted with the alcohol group on at least one of the reactive components.

In some embodiments, the present invention comprises ophthalmic compositions comprising at least one esterified omega-three fatty acid. In some embodiments, the present invention comprises ophthalmic compositions comprising at least one esterified omega-six fatty acid. In some embodiments, the present invention comprises ophthalmic compositions comprising at least one esterified omega-six fatty acid and at least one esterified omega-three fatty acid.

It is a benefit of the present invention that the esterified anti-inflammatory lipid mediators are hydrolytically stable at neutral pH, and do not hydrolyze during storage in the pH neutral ophthalmic composition and sterile preparations of the present invention. This means that the ophthalmic solutions and sterile preparations do not cause stinging when instilled in the eye. Upon contact with the cellular membranes and/or transport into the cells of the ocular surface, and without intending to be bound by theory, it is thought that esterified anti-inflammatory lipid mediators, such as esterified polyunsaturated fatty acids, esterified resolvins or a metabolically stable analog, esterified protectins or a metabolically stable analog, esterified lipoxins or a metabolically stable analog, esterified prostaglandins or a metabolically stable analog, esterified retinoic acids, endocannabinoids, and phospholipids, undergo hydrolysis and return to their acidic anti-inflammatory lipid mediator state along with the alcohol that was used in forming the ester.

The amounts of the esterified anti-inflammatory lipid mediator can be stated as a percentage of the total composition or as a percentage of the solution used in a processing step such as a lens hydration step (part of the lens making process that can result in the incorporation of the material into the device). The percentage of esterified anti-inflammatory lipid mediator can be determined by any method, but can, for example, be determined by dividing the weight of the anti-inflammatory lipid mediator by the total weight of the ophthalmic composition or device. The percentage of any component of the ophthalmic composition can be determined in a similar manner.

The amount of esterified anti-inflammatory lipid mediator which may be present in the ophthalmic compositions or devices of the present invention include from about 0.025 weight % to 5.0 weight % based upon all the components in the ophthalmic composition. When the ophthalmic composition is a rewetting drop, the esterified anti-inflammatory lipid mediator is present in an amount from about 0.025 weight % to 0.5 weight % based upon all of the components in the composition, and the acid content can be no more than 0.1 weight % (or 0.075, or 0.05, or 0.025, or even 0.01 weight %). When the ophthalmic composition is incorporated onto a contact lens, the esterified anti-inflammatory lipid mediator is present in an amount from 0.025 weight % to 5.0 weight % based upon all of the components in the composition, and the acid content can be no more than 1 weight % (or 0.75, or 0.5, or 0.25, or even 0.1 weight %).

In some embodiments, the invention is directed to the topical application of a composition comprising an esterified anti-inflammatory lipid mediator (e.g., esterified ALA) as an effective therapeutic strategy to decrease ocular surface inflammation. As discussed herein the inflammation of the ocular surface can be seen in, for example, dry eye syndrome and other inflammatory ocular conditions including, but not limited to, both anterior segment/front of the eye conditions and back of the eye conditions (e.g., meibomian gland dysfunction, blepharitis, atopic keratoconjunctivitis, contact lens related dry eye, Sjögren's syndrome, uveitis, macular degeneration, and a wide range of other conditions).

In another embodiment, the invention is directed to the topical application of a composition comprising an esterified anti-inflammatory lipid mediator (e.g., esterified ALA) as an effective strategy to improve tear film function or tear film stability. Without intending to be bound by theory, it is thought that the esterified anti-inflammatory lipid mediator improves the interaction between the lens and the tear film and/or the lids.

The present invention can also be administered to an individual that has been identified in need thereof of a composition described herein. The individual can be in need thereof, if the individual has been identified as suffering or having the condition of dry eye syndrome or one of the other inflammatory ocular conditions identified above. One in skill in the art would know how to identify the individual in need of a treatment for dry eye syndrome.

The present invention can also be administered to an individual to mitigate at least one sign and/or symptom of dry eye, or to provide osmoprotection to an individual in need thereof.

Without intending to be bound by theory, it is thought that when the anti-inflammatory lipid mediator composition is loaded onto a contact lens for delivery to the eye during contact lens wear, by virtue of its anti-inflammatory properties and the benefit provided to the tear film, the anti-inflammatory lipid mediator can be held on to the eye via the contact lens long enough to be delivered efficiently to the eye in order provide relief to individuals suffering from dry eye or other inflammatory ocular conditions.

Epithelial Construct Method

A model was developed to allow for the prediction of acute ocular discomfort obtained with fatty acid rewetting drops. The model uses a corneal epithelium tissue construct (e.g. HCE construct manufactured by SkinEthic). This tissue construct is formed by a full thickness corneal epithelium tissue reconstituted in vitro whereby human corneal epithelial cells were cultured at the air liquid interface in a chemically-defined medium, resulting in the formation of a corneal epithelial tissue devoid of stratum corneum and resembling histologically the mucosa of the human eye (Nguyen, D. H., et al., *Three-dimensional construct of the human corneal epithelium for In Vitro toxicology*. In: Alternatives Toxicological Methods. Boca Raton, Fla., CRC Press ed Katz S A and Salem H, 2003. Chapter 14: p. 147-159). The tissue is approximately 70 microns thick and has been shown to express the relevant markers of the fully differentiated corneal epithelial tissue (Nguyen et al, 2003).

The construct was further characterized, whereby dose-dependent effects of the common ophthalmic preservative benzalkonium chloride (BAK) were evaluated in terms of both cell viability impact and inflammatory cytokine release/cell activation. It was shown that the cell viability response in the model was consistent with the known in vivo effects of the BAK within the range of concentration that was evaluated. The cytokine endpoint (quantification of II-1 alpha release in the tissue culture media) allowed sensitive evaluations of the effects of the ophthalmic preservative on cell activation considering it allowed to discriminate non-cytotoxic concentrations of BAK (0.001 and 0.01%).

The esterified anti-inflammatory lipid mediator dose-responses were then evaluated in the construct, whereby 30 microliters of the rewetting drop was topically applied to the tissue for 8 or 24 hours, and cell viability was then quantified along with a subset of selected potential biomarkers within the tissue culture media. In vitro endpoints were probed for their correlation with the in vivo response (comfort upon instillation) in order to identify AOD predictors and define the (acute ocular) comfort prediction model.

It was determined that the 8 hour incubation period was the most relevant for optimal correlation between the in vitro and the in vivo responses. Using the 8 hour exposure condition, a very good correlation was obtained between the in vivo response of comfort upon instillation, measured immediately upon instillation, using a scale of 0 to 50, with 50 being the most comfortable score with a comfort rating of "Excellent," with a score of approximately 42 having a comfort rating of "Good," with a score of approximately 33 having a comfort rating of "better than satisfactory" (i.e., above average), with a score of approximately 26 having a comfort rating of "satisfactory" (i.e., average), with a score of approximately 18 having a comfort rating of "less than satisfactory" (i.e., below average), with a score of approximately 8 having a comfort rating of "poor," and 0 being the least comfortable score with a comfort rating of "very poor," and the following in vitro endpoints.

Table 1 shows the cell viability as assessed using the MTT assay.

TABLE 1

| Comfort Score Average | Cell Viability (% of PBS control) |
|---|---|
| 45 +/− 7 | 105 +/− 2 |
| 41 +/− 9 | 99 +/− 6 |
| 27 +/− 14 | 65 +/− 6 |
| 5 +/− 7 | 7 +/− 1 |

Table 2 shows Il-1 alpha release in the tissue culture media.

TABLE 2

| Comfort Score Average | Il-1 Average (% of PBS response) |
|---|---|
| 45 +/− 7 | 443 +/− 20 |
| 41 +/− 9 | 709 +/− 37 |
| 27 +/− 14 | 1276 +/− 109 |
| 5 +/− 7 | 3374 +/− 283 |

Table 3 shows Il-1 Ra release in the tissue culture media.

TABLE 3

| Comfort Score Average | Il-1 Ra Average (% of PBS response) |
|---|---|
| 45 +/− 7 | 123 +/− 3 |
| 41 +/− 9 | 235 +/− 6 |
| 27 +/− 14 | 386 +/− 25 |
| 5 +/− 7 | 917 +/− 22 |

The desired outcome of in vitro response was defined based on the in vitro-in vivo correlations. The undesirable comfort score corresponded to a score equal to or below 25, which translated into an undesirable cell viability in vitro endpoint of 60% or below, per in vivo-in vitro correlations. The most desirable comfort score was 35 or above, which translated into a cell viability value of 80% or above, per in vivo-in vitro correlations.

The model was further confirmed by showing that the alpha linolenic acid ethyl ester, which had shown a beneficial in vitro response in the model, also showed a beneficial response on the eye (i.e. lack of acute ocular discomfort).

The invention is now described with reference to the following examples. Before describing several exemplary embodiments of the invention, it is to be understood that the invention is not limited to the details of construction or process steps set forth in the following description. The invention is capable of other embodiments and of being practiced or being carried out in various ways.

EXAMPLES

Example 1

Topical compositions were formed by adding ethyl linolenate (alpha-linolenic acid ethyl ester (ALA-EE)), an esterified anti-inflammatory lipid mediator (AILM) having the formula:

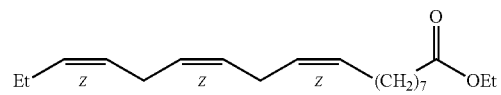

to a packing solution/aqueous-based delivery system containing various surfactants/emulsifiers, wetting agent, and a chelant and antioxidant(s) followed by mixing at high shear rate, to provide an emulsion suitable for topical application. Table 4 summarizes the ingredients of compositions.

TABLE 4

| | Example 1A | Example 1B | Example 1C | Example 1D |
|---|---|---|---|---|
| Modified packing solution[a] (wt %) | 99.3 | 94.8 | 94.8 | 94.9 |
| Glucam E20 (wt %) | 0.25 | 2.5 | 2.5 | 2.5 |
| Tween-80 (wt %) | 0.25 | 2.5 | 2.5 | 2.5 |
| ALA-EE (wt %) | 0.20 | 0.20 | 0.20 | 0.10 |
| Vitamin E (wt %) | 0.03 | 0.03 | 0.03 | 0.03 |

[a] = 0.4 wt % boric acid, 0.2 wt %, sodium borate, 0.5 wt % sodium chloride, 0.01 wt % Diethylenetriaminepentaacetic Acid (DTPA)

Example 2

Comparative

Topical compositions were formed by adding alpha-linolenic acid (ALA) to a packing solution/aqueous-based delivery system containing various surfactants/emulsifiers, wetting agent, and a chelant and antioxidant(s) followed by mixing at high shear rate, to provide an emulsion suitable for topical application. Table 5 summarizes the ingredients of compositions.

TABLE 5

| | Example 2A | Example 2B | Example 2C | Example 2D |
|---|---|---|---|---|
| Modified packing solution[a] (wt %) | 99.3 | 99.4 | 94.8 | 94.9 |
| Glucam E20 (wt %) | 0.25 | 0.25 | 2.5 | 2.5 |
| Tween-80 (wt %) | 0.25 | 0.25 | 2.5 | 2.5 |
| ALA (wt %) | 0.20 | 0.10 | 0.20 | 0.10 |
| Vitamin E (wt %) | 0.03 | 0.03 | 0.03 | 0.03 |

[a] = 0.4 wt % boric acid, 0.2 wt %, sodium borate, 0.5 wt % sodium chloride, 0.01 wt % Diethylenetriaminepentaacetic Acid (DTPA)

Example 3

Testing

The compositions of Examples 1A and 1B and Comparative Example 2A were tested in vitro as follows. A transepithelial permeability in vitro model (TEP test) was used to assess fluorescein leakage (or increased transepithelial permeability) with the free acid in comparison with the ester form of the alpha linolenic acid. Results are provided in Table 6, which shows that the ALA ethyl ester at high concentration (0.2%) behaved similarly to the vehicle (packing solution with Tween and Glucam) in terms of the effect on transepithelial permeability, whereas the ALA fatty acid showed a significant increase in fluorescein leakage at the same concentration, relative to the controls, that was consistent with the clinical observation of discomfort upon instillation. This suggests that the ester version of the omega-three fatty acid will have an improved tolerability profile upon instillation compared to the use of the free acid when using concentrations as high as 0.2%.

TABLE 6

|  | Fluorescein leakage (Fluorescence units) |
|---|---|
| HBSS Buffer | 936 +/− 280 |
| Packing Sol'n | 847 +/− 373 |
| Vehicle 0.25% TW$^c$ and Glcm$^d$ | 572 +/− 514 |
| Example 2A | 14004 +/− 5544 |
| Example 1A | 545 +/− 462 |
| Example 1B | 720 +/− 531 |

$^c$TW is Tween-80
$^d$Glcm is Glucam E20

Example 4A

Testing

The compositions of Examples 1C, 1D and Comparative Examples 2C, 2D were tested in vitro as follows. A corneal epithelial tissue model consisting of a multi-endpoint assay system whereby the cell viability was evaluated in addition to the measurement of biomarkers or specific cytokines which were previously shown (see tables 1-3 with corresponding correlation curves) to correlate with the in vivo data of subjective discomfort (upon instillation). Results for 8 hours are provided in Table 7A, which shows that the ethyllinolenate (ALA-EE) had 10 times less impact on the in vitro endpoint (after 8 hour exposure) than the linolenic acid (ALA), suggesting that ALA-EE may be used at concentrations of up to 0.2% or higher without inducing initial discomfort upon instillation.

TABLE 7A

|  | Cell viability (% of PBS ctrl) | Form of AILM | Acid/Ester Concentration |
|---|---|---|---|
| Vehicle | 105 +/− 2 | N/A | N/A |
| Example 1C | 70 +/− 8 | Ester | 0.2 wt % |
| Example 1D | 81 +/− 1 | Ester | 0.1 wt % |
| Example 2C Comparison | 7 +/− 1 | Acid | 0.2 wt % |
| Example 2D Comparison | 65 +/− 6 | Acid | 0.1 wt % |

Example 4B

Testing

The compositions of Example 1C (ALA-EE 0.2%) and Comparative Example 2C (ALA 0.2%) were tested in vitro using SkinEthic 0.1 cm$^2$ human corneal epithelium tissue constructs (HTS constructs) and 24 hours exposure time point. The results are shown in Table 7B, below.

Overall, the in vitro data of Examples 3, 4A, and 4B indicate that the ester version of the omega three fatty acid is much less likely to cause initial discomfort upon instillation, compared to the free acid and that its use would offer the advantage to allow the use of a higher concentration (for efficacy) without any risk of causing initial discomfort response.

TABLE 7B

|  | Cell viability (% of PBS ctrl) | Il-1 alpha (pg/ml) | Form of AILM | Acid/Ester Concentration |
|---|---|---|---|---|
| Vehicle | 75.75 +/− 7.17 | 152.75 +/− 20.15 | N/A | N/A |
| Example 2C Comparative | 3.73 +/− 1.38 | 809.25 +/− 240.77 | Acid | 0.2 wt % |
| Example 1C | 87.00 +/− 7.63 | 112.48 +/− 0.04 | Ester | 0.2 wt % |
| PBS | 100.00 +/− 5.98 | 31.63 +/− 4.00 | N/A | N/A |

Example 5

Preliminary non-dispensing clinical studies were conducted to further assess the use of omega-three fatty acid compositions. A 0.05 wt. % concentration ester version of an omega-three fatty acid was instilled on three "contact lens induced dry eye" subjects (each with at least one sign and one symptom of contact lens induced dry eye) without any acute ocular discomfort or physiological findings. Similarly a 0.2 wt. % concentration ester version of the omega-three fatty acid was instilled on four "contact lens induced dry eye" subjects without any acute ocular discomfort or physiological findings.

Example 6

Omega-three ester material (notably, the alpha linolenic acid ethyl ester (ALA-EE) or ethyl linolenate) was loaded into a contact lens for its slow delivery on the eye during contact lens wear. By virtue of its anti-inflammatory properties and the benefit it might provide to the tear film, the omega-three fatty acid (ester) can be held on the eye via the contact lens long enough to be delivered efficiently to the eye in order to provide relief in subjects suffering from dry eye or other inflammatory conditions. Conditions targeted by this material include both anterior segment/front of the eye conditions and back of the eye conditions, whereby the slow delivery of the omega-three fatty acid (ester) may provide protection against diseases such as macular degeneration or may delay the onset of the condition, by virtue of the materials' antioxidant and anti-inflammatory properties.

It is believed that the use of the ester form of the omega-three fatty acid derived from reaction with a monohydric alcohol provides the benefit of improving bioavailability and allows for an on-eye release of the acid form upon encounter with the ocular tissue esterases. In the following examples, the omega-three ester material was the linolenic acid ethyl ester or ethyl linolenate.

ALA-EE was dissolved in isopropanol (IPA) at the concentration of 0.05 or 0.5%. Silicone hydrogel contact lenses (senofilcon, commercially available as ACUVUE® OASYS® with HYDRACLEAR® Plus lenses) were then allowed to soak in the ALA-EE-containing IPA for up to 1 hour at room temperature, followed by soaking in ALA-EE containing IPA/packing solution (70% IPA/30% packing solution) for up to 1 hour, rinsing in packing solution, and packaging of lenses in the packing solution. ALA-EE uptake by the contact lenses was quantified by gas chromatography. No quantifiable free acid form was associated with the lenses, showing that the ALA-EE did not hydrolyze to the free acid form under these conditions (Table 8).

ALA-EE uptake was 54 and 611 micrograms per lens using 0.05 and 0.5% ALA-EE solution in IPA, respectively (Table 6).

TABLE 8

| | % ALA-EE in IPA solution | ALA-EE (µg/lens) | ALA (µg/lens) |
|---|---|---|---|
| Example 6A | 0.05 | 53.7 +/− 3.8 | BDL* |
| Example 6B | 0.5 | 610.6 +/− 6.6 | BDL* |

*BDL: below detection limit.

Example 7

Comparative

A comparative silicone hydrogel contact lens that incorporated alpha linolenic acid (ALA), rather than the ester, was prepared following the same protocol as Example 6. The uptake of ALA by the contact lenses was 23 and 300 micrograms per lens, when using a 0.05% and 0.5% ALA solution in IPA, respectively (see Table 9).

TABLE 9

| | % ALA in IPA solution | ALA (µg/lens) |
|---|---|---|
| Example 7A | 0.05 | 22.9 +/− 1.6 |
| Example 7B | 0.5 | 299.0 +/− 16.5 |

Example 8

Testing

The evaluation of the ALA and ALA-EE lenses of Examples 6 and 7 in a reconstituted human corneal epithelium construct showed a favorable interaction with the ocular surface tissue following a 24 hour exposure, in terms of the absence of impact on cell viability. The cell viability was not reduced relative to phosphate buffered saline (PBS) negative control (Table 10).

TABLE 10

| | Cell viability (% of PBS ctrl) |
|---|---|
| Example 6B | 105 +/− 2 |
| Example 7B | 95 +/− 7 |
| Control (no treatment) | 110 +/− 1 |
| PBS ctrl 24 hour | 100 +/− 9 |

In Examples 4A and 4B, it was shown that the ester form of the omega-three fatty acid (ethyl linolenate) allowed the use of a higher concentration of the material within a rewetting drop emulsion without causing an initial discomfort.

In this example, it was demonstrated that the ester form of the omega-three fatty acid (ethyl linolenate) can be loaded at higher quantities than the free acid form using the same concentration of the raw material. Lenses incorporating such high amounts of the ester form of the omega-three fatty acid did not yield any loss in cell viability, suggesting acceptable ocular tolerability of the product.

Other methods of incorporation of the ethyl linolenate included the use of propylene glycol hydration (ALA-EE was solubilized into propylene glycol instead of IPA for the hydration/soaking of the lenses) and it was verified that no major changes in lens parameters were observed.

Example 9

The alpha linolenic acid ethyl ester (ALA-EE) was dissolved in propylene glycol (PG) at concentrations of 0.05 and 0.5%, and silicon hydrogel lenses (Narafilcon B lenses (ACUVUE® TrueEye®)) were hydrated or soaked in the ALA-EE-containing propylene glycol solution for one hour at room temperature, followed by rinsing in DI water and repackaging of lenses in the packing solution. The lenses were packaging in borate buffer packing solution with 50 ppm methyl cellulose and autoclaved at 121° C. for 19 minutes. ALA-EE was quantified by gas chromatography.

Under these conditions and using the narafilcon B substrate, ALA-EE uptakes were 91 and 721 micrograms per lens using 0.05 and 0.5% ALA-EE solution, respectively, in IPA, respectively (Table 11). There was no detectable hydrolysis of the ester to the acid under these conditions.

TABLE 11

| | % ALA-EE in PG solution | ALA-EE (µg/lens) | ALA (µg/lens) |
|---|---|---|---|
| Example 9A | 0.025 | 51.7 +/− 3.7 | BDL* |
| Example 9B | 0.05 | 91.0 +/− 10.6 | BDL* |
| Example 9C | 0.5 | 721.5 +/− 39.3 | BDL* |

*BDL: below detection limit.

There was no change in water content or lens diameter under these conditions.

Example 10

Testing

The release of ALA-EE from selected lenses of Example 9 was assessed both in vitro and in vivo (rabbit study), In vitro release in 1 ml of 2.5% Tween-80 in packing solution showed that 50% of the ALA-EE was released from a lens according to Example 9A within 3 days.

For in vivo testing, an animal study was conducted to evaluate ocular tolerability of the product, and in particular, to assess in vivo release rates. In vivo release in rabbit eyes showed a relatively slow release of the ALA-EE over time. With respect to a lens according to Example 9B, 43% of the ALA-EE was released within the first 12 hours, with an average of 3 micrograms per hour after the first hour. Over the course of one day, approximately 40 to 50 micrograms was released from the narafilcon B lens.

Examples 11-12

ALA-EE was dissolved in propylene glycol (PG) at concentrations of 0.05 and 0.1%, and silicone hydrogel lenses (narafilcon B lenses (ACUVUE® TrueEye®)) were soaked at ambient temperature in the PG-ALA-EE solutions (200 lenses per liter of solution) with constant agitation for 1 hour. The lenses were rinsed twice with water at ambient temperature for 30 minutes. The lenses were packaging in borate buffer packing solution with 50 ppm methyl cellulose and autoclaved at 121° C. for about 19 minutes.

The lenses were worn for 8-12 hours by 7-8 human patients. No discomfort was reported, and no adverse events or clinically significant corneal staining or deposition was noted. Wettability was uniform at dispensing. Mild to trace non-uniform wettability was noted in some patients at the follow-up visit.

All worn lenses were collected. The residual levels of ALA-EE were extracted using methylene chloride and quantified via gas chromatography. The lenses contacted with 0.05% ALA-EE had an average of 27 ug released and the lenses contacted with the 0.1% ALA-EE had an average of 51 ug released over the wear time, respectively. This corresponded to a rate of release of 3.7 and 6.4 ug/hour, assuming linear release rate.

Example 13

Using animal data from a dry eye mouse model for rewetting drops containing a fatty acid, it is estimated that a 4 drops per day dosage of a 0.2% ALA rewetting drop would equate to cumulated dose of 40 micrograms applied to the ocular surface, taking into account the assumptions that a drop represents 50 microliters and that 90% of the drop is lost and only 10% is retained initially on the eye (due to initial loss upon drop application/initial drainage).

It is believed that the ester or amides of anti-inflammatory lipid mediator disclosed in the present application, have similar delivery concentrations to the ocular environment as the fatty acids. Thus, a similar range of amount of ALA-EE made available to the ocular surface upon use of a contact lens loaded with 90 micrograms ALA-EE. Considering higher retention time on the eye during the use of the lens, such amounts of ALA-EE released may thus provide better efficacy than when using a rewetting drop.

Reference throughout this specification to "one embodiment," "certain embodiments," "one or more embodiments," "further embodiment," or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. An ophthalmic device for the treatment of ocular conditions comprising:
    a hydrogel contact lens incorporating an ester of an anti-inflammatory lipid mediator that is a reaction product of the anti-inflammatory lipid mediator and a monohydric alcohol selected from the group consisting of eicosapentaenoic acid ethyl ester and alpha-linolenic acid ethyl ester and mixtures thereof;
    wherein the ophthalmic device is contained in a sealed package in which the contact lens incorporating the ester of the anti-inflammatory lipid mediator is stored in the presence of a packing solution.

2. The ophthalmic device of claim 1, wherein the ester or amide is present in the contact lens in a therapeutically effective amount.

3. The ophthalmic device of claim 1, wherein the ester is present in the contact lens in an amount in the range of about 0.01% to 0.5% by weight.

4. The ophthalmic device of claim 1, wherein the packing solution is water-based.

5. The ophthalmic device of claim 4, wherein the packing solution further comprises one or more of the following: methyl cellulose, a surfactant, a wetting agent, a chelant, and an antioxidant.

6. The ophthalmic device of claim 5, wherein the packing solution comprises one or more ingredients selected from the group consisting of methyl cellulose, Tyloxapol™, methyl gluceth-20, Vitamin E, diethylenetriaminepentaacetic acid, boric acid, sodium borate, and sodium chloride.

7. The ophthalmic device of claim 1, wherein upon wearing of the contact lens on-eye, the ester releases over time.

8. The ophthalmic device of claim 7 comprising a release rate of approximately 3 micrograms per hour after a first hour of wearing.

9. The ophthalmic device of claim 1, wherein the ester is incorporated into the contact lens in an amount in the range of about 50 to about 620 micrograms per lens.

10. The ophthalmic device of claim 1, wherein the hydrogel contact lens is selected from the group consisting of balafilcon, acquafilcon, lotrafilcon, comfilcon, galyfilcon, senofilcon, narafilcon, falcon II 3, or asmofilcon A.

11. The ophthalmic device of claim 1 wherein the ester is eicosapentaenoic acid ethyl ester.

12. The ophthalmic device of claim 1 wherein the ester is alpha-linolenic acid ethyl ester.

* * * * *